United States Patent [19]

Johnsen et al.

[11] 3,954,725

[45] May 4, 1976

[54] ALCOHOL SOLUBLE ACYLATED PROTEIN HYDROLYZATE REACTION PRODUCTS

[75] Inventors: Vernon L. Johnsen; Thomas M. Weisinger, both of La Grange, Ill.

[73] Assignee: Wilson Pharmaceutical & Chemical Corporation, Chicago, Ill.

[22] Filed: May 17, 1974

[21] Appl. No.: 470,740

Related U.S. Application Data

[63] Continuation of Ser. No. 234,410, March 13, 1972, abandoned.

[52] U.S. Cl. ............................ 260/112 R; 260/117; 260/123.7; 424/DIG. 1; 424/DIG. 2; 424/47; 424/70; 424/71; 132/7
[51] Int. Cl.² ...................... C07G 7/00; C09H 7/00
[58] Field of Search ............... 260/112 R, 117, 121, 260/123.7, 123.5

[56] References Cited
UNITED STATES PATENTS

| | | | |
|---|---|---|---|
| 2,015,912 | 10/1935 | Sommer | 260/121 |
| 2,041,265 | 5/1936 | Orthner et al. | 260/112 X |
| 2,100,090 | 11/1937 | Sommer et al. | 260/121 X |
| 2,113,819 | 4/1938 | Tucker | 260/117 X |
| 2,119,872 | 6/1938 | Wiegand | 260/121 X |
| 2,151,241 | 3/1939 | Sommer et al. | 260/121 X |
| 2,609,300 | 9/1952 | Storrs et al. | 260/123.5 X |
| 2,712,539 | 7/1955 | Nugent et al. | 260/123.5 |
| 2,728,759 | 12/1955 | Keil | 260/112 |
| 3,004,021 | 10/1961 | Selle et al. | 260/112 X |
| 3,394,119 | 7/1968 | Luce et al. | 260/112 |

*Primary Examiner*—Howard E. Schain

[57] ABSTRACT

An acyl amide product of reaction of polypeptides useful in cosmetics such as hair sprays because it is alcohol soluble and forms continuous films which are insoluble in water of neutral or acidic pH, is prepared by hydrolyzing proteins with either alkali metal hydroxides or calcium hodroxide mixture, bonding to the hydrolyzate an acyl radical selected from the group consisting of 12, 14, 16 and 18 carbon atoms through amide linkages to produce reaction products of for example, alkali metal hydrolyzates, the reaction products of the respective acyl radicals having an average total molecular weight in the ranges of 433 to 583; 386 to 486; 389 to 489; and 392 to 467.

3 Claims, No Drawings

ALCOHOL SOLUBLE ACYLATED PROTEIN HYDROLYZATE REACTION PRODUCTS

This is a continuation, of application Ser. No. 234,410, filed Mar. 13, 1972 and now abandoned.

This invention relates to derivatives of protein hydrolyzates having unique properties. More particularly it relates to a process for modifying protein hydrolyzates to adapt them to use as a water-insoluble alcohol soluble component of cosmetics. Still more particularly, it relates to products having as one component a polypeptide mixture of an average molecular weight in a specific range and as the second component an acyl radical selected from the group having of 12 to 18 carbon atoms, joined together by amide linkages to produce alcohol soluble-reaction products suitable for use in the care of human hair where film forming is a necessary requirement, i.e., in hair lotions, sprays, and the like.

Briefly, the amide form of polypeptide derivatives of the present invention comprises a reaction product of a hydrolyzate of proteins selected from the group of alkali metal hydrolyzate and calcium hydroxide hydrolyzate having chemically bonded thereto an acyl radical selected from the group consisting of 12, 14, 16 and 18 carbon atoms, said reaction product having an average total molecular weight in the range of 433 to 583 when prepared from a alkali metal hydrolyzate and having a 12 carbon atom acyl radical, having an average total molecular weight in the range of 386 to 486 when prepared from a alkali metal hydrolyzate and having a 14 carbon atom acyl radical, having an average total molecular weight in the range of 389 to 489 when prepared from a alkali metal hydrolyzate and having a 16 carbon atom acyl radical, having an average total molecular weight in the range of 392 to 467 when prepared from a alkali metal hydrolyzate and having a 18 carbon atom acyl radical, having an average total molecular weight in the range of 633 to 743 when prepared from a calcium hydroxide hydrolzyate and having a 12 carbon atom acyl radical, having an average total molecular weight in the range of 560 to 568 when prepared from a calcium hydroxide hydrolyzate and having a 14 carbon atom acyl radical, having an average total molecular weight in the range of 464 to 564 when prepared from a calcium hydroxide hydrolyzate and having a 16 carbon atom acyl radical, and having an average total molecular weight in the range of 417 to 517 when prepared from a calcium hydroxide hydrolyzate and having a 18 carbon atom acyl radical.

Acyl amide reaction products having a proper balance of polypeptide molecular weight and acyl group molecular weight possess alcohol solubility as a novel characteristic. Homogeneous alcohol solutions of the acyl amide reaction products of the instant invention exhibit the novelty of being compatible with aerosol propellants. In addition, when alcohol solutions of such reaction products are applied to filamentous materials such as human or animal hair and the solvents are evaporated, the deposited reaction products exhibits the unique characteristic of forming a continuous flexible film which is water-insoluble. Another unique characteristic of the alcohol soluble reaction products is that the deposited films are water-insoluble and non-hygroscopic but are dissolvable in aqueous mediums of near neutral or alkaline pH as in any standard soap or detergent solution.

For many uses of proteinaceous materials for example, in cosmetic products, gelatin meets the color and odor requirements but the viscosity and stable gel forming ability produces an undesirable texture.

One type of attempt to improve the character of gelatin for cosmetic uses, for example, in hair grooming compositions, has been hydrolysis of the proteinaceous materials. The disadvantages of such hydrolyzed proteins has been the brittleness of the films when dry and their hygroscopicity when exposed to a humid atmosphere and they are insoluble in anhydrous alcohol which precludes their use in conventional aerosol hair spray.

Modification of protein hydrolyzate by reacting polypeptides of less than about 150 molecular weight contained in an organic solvent in an alkaline medium; with mixture of fatty acids derived from coconut oil to produce detergents, has been described in U.S. Pat. No. 2,113,819. These reaction products are water soluble and foam strongly and are not depositable as continuous films on filamentous materials, etc.

Now it has been discovered that acyl amide forms of polypeptide derivatives having utility as a grooming agent in aliphatic alcohol base compositions, which can be deposited on human hair as non-hygroscopic films can be prepared by the method which comprises chemically bonding an acyl radical selected from the group consisting of 12, 14, 16 and 18 carbon atoms by reaction in an alkaline aqueous solution to a hydrolyzate selected from the group consisting of a alkali metal hydroxide and calcium hydroxide hydrolyzate through an amide linkage to produce reaction products of an average total molecular weight in the range of 433 to 583 when prepared from a alkali metal hydrolyzate and having a 12 carbon atom acyl radical, having an average total molecular weight in the range of 386 to 486 when prepared from a alkali metal hydrolyzate and having a 14 carbon atom acyl radical, having an average total molecular weight in the range of 389 to 489 when prepared from a alkali metal hydrolyzate and having a 16 carbon atom acyl radical, having an average total molecular weight in the range of 392 to 467 when prepared from a alkali metal hydrolyzate and having a 18 carbon atom acyl radical and having an average total molecular weight in the range of 633 to 743 when prepared from a calcium hydroxide hydrolyzate and having a 12 carbon atom acyl radical, having an average total molecular weight in the range of 560 to 685 when prepared from a calcium hydroxide hydrolyzate and having a 14 carbon atom acyl radical having an average total molecular weight in the range of 464 to 564 when prepared from a calcium hydroxide hydrolyzate and having a 16 carbon atom acyl radical, having an average total molecular weight in the range of 417 to 517 when prepared from a calcium hydroxide hydrolyzate and having a 18 carbon atom acyl radical.

More in detail, the method comprises adding to an aqueous solution of a hydrolyzate of proteins selected from the group consisting of alkali metal hydrolyzate and calcium hydroxide hydrolyzate, a fatty acid chloride in amounts constituting up to about 10% excess over the stoichiometric equivalent amount based upon the free amino groups of said hydrolyzate, said fatty acid reactant making available for amide linkage to the polypeptides an acyl radical selected from the group consisting of 12, 14, 16 and 18 carbon atoms maintaining the pH of the aqueous solution in the range between 7.5 and 12.5 and the temperature in the range between about 70°F. and 180°F. until the amide reaction is indicated complete by a nonchanging pH segregating water-insoluble fatty acid reactants from the solution of reaction products by precipitation effected by first adjusting the pH to between about 5 and 6.5 to remove unreacted fatty acid, then adjusting the pH of the fatty acid reactant free solution of the reaction products to between 2 and 4 to precipitate the reaction products, recovering the precipitate acyl amide polypeptide reaction product, of average total molecular weight hereinbefore set forth, washing said precipitate to remove water soluble contaminants, dehydrating said washed precipitate. isolating the alcohol soluble portion of said precipitate by mixing said precipitate with ethyl alcohol, removing insoluble components from the alcohol solution, utilizing the reaction product as an alcoholic solution or recovering the soluble reaction product from the alcohol solution.

The acyl amide derivatives of the polypeptide mixtures, having a proper balance of components productive of predominantly alcohol soluble derivatives, are insoluble in water at the natural pH induced by the free carboxyl group of the amide reaction product, i.e., water which is not buffered with alkaline agents. The reaction products having a proper balance of the molecular weight of the polypeptide component relative to the $C_{12}$ to $C_{18}$ acyl group form flexible non-hygroscopic coatings or films when deposited from the alcohol solution.

The reaction products are prepared in dry form in accordance with this invention by hydrolyzing a protein, such as gelatin, proteins derived from collagen-containing material, etc, with an aqueous solution of alkalis selected from the group consisting of alkali metal hydroxides such as sodium, potassium, and lithium and of calcium hydroxide of a strength capable of breaking down the complex protein molecules to degradation products such as polypeptides and in some cases amino acids. The preparation of alcohol soluble acyl amide polypeptides requires the hydrolysis to be continued until the protein reaches the stage, at which the mixtures contain polypeptides which when reacted with fatty acids must fall within the hereinafter discussed ranges. Such mixtures are hereinafter identified as having an average molecular weight and the reaction products are identified as having an average total molecular weight.

The length of time required for hydrolysis will depend upon the temperature maintained and the concentration of hydrolysis agent. The temperature generally is maintained in the range between about 85°C. and 130°C. for a period of 1 to 5 hours when using for example, alkaline agents such as sodium hydroxide, calcium hydroxide, etc., in amounts constituting 30% to 10% by weight, based upon the amount of protein to be hydrolyzed. While appropriate polypeptide mixtures can be produced by using hydrolysis agents selected from the group consisting of alkali metal hydroxides and calcium hydroxide, the preferred procedure is hydrolysis utilizing calcium hydroxide because the mixtures produced thereby contain polypeptides of more uniform molecular weight and thus the derivative mixtures prepared with a particular acyl group will contain fewer derivatives of polypeptide components of molecular weight removed so far from the average molecular weight necessary to obtain satisfactory characteristics that portions of the derivatives will be either alcohol insoluble or have unsatisfactory characteristics. The elimination of such derivatives of molecular weight outside the specified ranges necessitates extensive purification treatments.

When the protein has been converted to a polypeptide mixture having average molecular weight in the various ranges capable of giving rise to reaction products of the hereinafter set forth ranges of average total molecular weight, hydrolysis is terminated by neutralization of the hydrolysis agent.

Determination of the Kejldahl nitrogen content and the Van Slkye amino nitrogen content, provides a basis for calculation of the average molecular weight of the polypeptide and the molecules of free amino groups which are available as reactive groups for formation of amide linkages.

Control of the temperature of the solution during the amide forming reaction is one of the factors necessary in order to obtain a satisfactory yield. Accordingly, the temperature of the solution is maintained in the range between abouut 15°C. and 50°C.

Aqueous solution of the polypeptide mixture to be reacted with the fatty acid reactant is adjusted, if necessary, to an alkaline pH, preferably in the range between about 8 and 10. Fatty acid chloride is added to the pH adjusted solution in at least the stoichiometric amount for conversion of the free amino groups of the polypeptide mixture to amide linkages for bonding the polypeptide and acyl components of the reaction products.

Typical fatty acid reactants are fatty acid halogens such as lauryl chlorides, myristyl bromide, palmityl iodide, stearyl chloride, etc.

When using fatty acid chlorides as the reactant in aqueous mediums, an amount constituting up to approximately 10% excess over the stoichiometric requirement has been found to yield products having uniformity of properties.

During the acyl amide forming reaction, a lowering of the pH of the reaction mixture solution occurs. The pH is prevented from lowering to less than 7.5 by repetitive additions of sodium hydroxide. When the pH is exhibiting stability by remaining substantially constant, a stage reached generally after a period of 30 minutes, completion of the amide forming reaction is indicated.

Upon completion of the amide forming reaction, the reaction mixture pH is adjusted with mineral acids such as sulfuric hydrochloric or phosphoric acid, to a pH of about 6 and the suspension filtered to remove insoluble uncombined fatty acids. The recovered solution of reaction products is further adjusted in pH to between about 2 and 4 to precipitate the reaction products. The precipitated reaction products are recovered by suitable means such as filtering, decantation, etc. The solids are washed to remove adhering soluble contaminants such as salts and unreacted polypeptides and the washed reaction product dehydrated. Dehydrated reaction product is mixed with a lower aliphatic alcohol such as methyl, ethyl and propyl alcohol to effect solution of the alcohol soluble portion of the reaction products and permit removal of any alcohol insoluble components and then the alcohol soluble reaction product can be utilized in the alcohol solution form or can be recovered from the alcohol solution as a dry powdered product.

In accordance with a preferred embodiment of the invention, 140 gram gelatin is dissolved in 360 cc water and 25.5 grams of calcium hydroxide in 82 cc water is added. After treatment for 6 hours at a temperature of about 190°F., a hydrolyzate may be formed whose components have an amino nitrogen content of 1.85%.

After cooling the solution which has a pH of about 10, sulfuric acid is added to it in quantities to lower the pH to approximately 8. 36 grams of lauryl chloride is added to the pH adjusted solution and the pH of the mixture is checked every 5 minutes and when the pH drops to 7.5, sodium hydroxide solution is added to maintain pH in the range of 8.0 to 9.0.

After approximately 2 ½ hours, the reaction is completed and sufficient sulfuric acid is added to adjust the pH of the solution to about 6. The solution then is filtered to remove insoluble unreacted fatty acid and the filtrate is adjusted to pH 3.0 At this pH, a solid material is precipitated. The precipitate is then washed thoroughly with water for removal of salts and unreacted polypeptide. This solid material having a preferred average total molecular weight in the range of 650 to 700 is recovered by suitable means as by settling, decantation of supernatant or filtering after which the product is dehydrated for example, by air drying for 3 days.

The problems involved in the use of film forming agents in cosmetics, such as spray for human hair, have been the need for such properties as non-hygroscopicity, water insolubility, flexibility of thin continuous films compatibility of alcohol solutions thereof with any supplemental agents and the propellants, such as Freons used in aerosol dispensers, and susceptibility of the films to removal from the human hair on the human head by shampoos so that accumulation of undesirable quantities of agent can be avoided.

Shellac is one of the well known film forming agents in that it is water-insoluble and provides a good film for holding a hair style. However, shellac causes an undesirable buildup because its resists removal by conventional shampoos.

Another well known commercially available hair spray contains polyvinyl pyrolidone. This resinous material while alcohol soluble and compatible with "Freon" (chlorinated and fluorinated hydrocarbons) propellants, is somewhat water soluble and loses its effectiveness in maintaining a hair style in humid atmospheres.

The amide products of this invention possess all of the desirable properties, namely, alcohol solubility, compatibility of alcohol solutions thereof with agents such as polyvinyl pyrolidone and the propellants, formation of continuous films, water insolubility of the films and ready conversion to water soluble salts, when the hair is treated with alkaline shampoos, which salts are then dissolved and removed in aqueous rinse mediums.

The alcohol solubility of a particular acyl amide derivative of polypeptides varies somewhat depending upon average molecular weight of the polypepetide component of the reaction products. When calculating total molecular weight of reaction products, total nitrogen is first measured and a factor of 6.25 is used to convert a nitrogen content to polypeptide moiety. In general, the greater the molecular weight of the acyl component, the lower the average molecular weight of the polypeptide component which will exhibit optimum alcohol solubility. Optimum alcohol solubility, for example, for the lauryl derivative, of an alkali metal hydrolysis polypeptide mixture is exhibited when the average total molecular weight of the reaction product is of the order of 475, whereas for the stearyl derivative, the average total molecular weight is of the order of 400. Accordingly, the preferred ranges of average molecular weight of alkali metal hydrolyzed polypeptide mixtures to be converted to lauryl amide derivatives is about 225 to 375, to myristyl amide derivatives is about 200 to 250, to palmityl amide derivatives is about 175 to 225 and to stearyl amide derivatives is about 150 to 175.

Utility of the acyl amide polypeptide derivatives depends not only upon alcohol solubility but upon ability to produce flexible films.

Inasmuch as polypeptide mixtures are the result of a reaction which breaks down large complex materials into a variety of smaller components of widely varying molecular weight, an average molecular weight for a hydrolysis product provides a basis for defining the polypeptide component of the acyl amide reaction product mixture which will consist of predominantly of alcohol soluble components. For example, a lauryl amide derivative of sodium hydroxide hydrolysis mixture of average molecular weight of about 365 will generally contain a negligible amount of components insoluble in ethyl alcohol containing 20% or 1% by weight of the lauryl amide polypeptide derivatives whereas a mixture of average molecular weight of above 400 will generally show significant amounts of components insoluble in alcohol solutions.

Due to variations in hydrolysis, the polypeptides mixture having an average molecular weight such that the average total molecular weight of the reactions products fall within the specified ranges, may contain some polylpeptides of molecular weight outside the minimum or maximum limits required for alcohol solubility and will produce some alcohol insoluble components when reacted to form acyl amide derivatives. The acyl amide derivative mixtures can be purified, i.e., insoluble components may be removed by slurrying the reaction product with alcohol and separating the undissolved solids from the solution phase.

The invention will be more fully illustrated and more readily understood from the following examples, which are intended to be illustrative only and are not to be construed as limitations on the invention.

EXAMPLE I 118 pounds of gelatin was dissolved in 37 gallons of water. 21.2 pounds of calcium hydroxide in 10 gallon water was incorporated in the solution and the solution heated to 190°F. for approximately 8 hours. Aliquots of the liquor resulting from the hydrolysis were subjected to the conventional Kejldahl and Van Slyke tests and the total nitrogen and amino nitrogen determined. The total nitrogen of the hydrolyzate on a solids basis was 16.4% and the amino nitrogen content on a solids basis 2.25%.

The hydrolyzate is adjusted to pH 9.0 with sulfuric acid and 64 pounds of palmityl chloride is added slowly over a period of 2 hours. Reaction is indicated by evolution of heat and drop in pH. When the pH dropped below 7.5, sodium hydroxide in the form of a 5% solution is added to maintain pH in the range of 7.5 to 10.0.

Upon completion of the reaction, as evidenced by a constant pH of 8, sulfuric acid solution is added to adjust the pH of the solution to 6. Insoluble elements are filtered from the acidified solution. The acidified solution filtrate is further acidified to a pH of 3 by mixing therein additional sulfuric acid solution. Finely divided solids form in the acidic solution of pH 3. The solids are separated from the liquid by filtration. Filtered solids are washed and the washed solids dried in a draft oven at a temperature of 150°F. then under vacuum, i.e., reduced pressure, of 20 mm of Hg absolute. Recovery of 35 pounds of dry reaction product establishes a yield of 30% based upon the dry weight of gelatin starting material.

The dried reaction product prepared had a solubility in ethyl alcohol at 20% by weight concentration of approximately 98%.

EXAMPLE II 440 pounds of gelatin was dissolved in 160 gallons of water. 165 pounds of 50% aqueous solution of sodium hydroxide was added to the solution and the solution heated at 190°F. for approximately 3 hours. An aliquot of the liquor resulting from hydrolysis was subjected to the conventional Kejldahl analysis and the Van Slyke test to determine the total and amino nitrogen content. The total nitrogen content of approximately 13.2% and the Van Slyke of 2.65% indicated a reduction in molecular weight of the proteins to an average value of about 350.

The pH of the hydrolyzed gelatin solution was reduced to 9.0 and 330 pounds of myristyl chloride was added over a period of 5 ½ hours. Reaction is indicated by evolution of heat and a drop in pH. When the pH dropped below 7.5, sodium hydroxide in the form of a 5% solution was added to raise pH to within the range of 7.5 to 10.0.

Upon completion of the reaction, as evidenced by a constant pH of 8, 10% hydrochloric acid was added to adjust the pH of the solution to 6. The solution was filtered to remove insoluble material and the filtrate was then adjusted to pH 3.0 with 10% hydrochloric acid solution. Finely divided solids form in the acidic solution. The solids were separated from the liquid by centrifugation. The solids were washed with acid solution of pH of about 3 and then were dried on a heated continuous steel belt dryer. Recovery of 290 pounds of dry reaction product establishes a yield of 66% based upon the dry weight of gelatin starting material.

The reaction product having an average total molecular weight of about 400 had a solubility in ethyl alcohol at 20% by weight of concentration of approximately 98%.

EXAMPLE III

A polypeptide was produced by subjecting collagen-containing material, such as pigs feet, to a cooking operation at about 230°F. for 2 hours in an aqueous medium containing calcium bisulfite to prevent development of a dark color in the liquor.

The liquor recovered after filtration is a straw colored solution of proteins whose gelling property has been eliminated by the treatment at a high temperature in the presence of water. The solution has a Formol Nitrogen value of about 5.6 and a pH of 6. The dry solids are a mixture of proteins having an average molecular weight of 10,000.

210 parts by weight of the dry solids were dissolved in 630 parts by weight of water. 84 parts by weight of calcium hydroxide slurried in 300 parts of water was added to the solution and the solution heated in 190°F. for 36 hours. The final hydrolysis material is a solution whose polypeptide content has a total nitrogen content of 16.4% and the Van Slyke amino nitrogen content of 5.1% indicating an average molecular weight of about 225.

The aqueous solution of hydrolyzed protein was adjusted in pH to about 10.0 and 309 parts by weight of stearyl chloride added to it over a period of 3 ½ hours and the reaction to form the acyl amide reaction product was carried out as described in Example I.

The amide reaction product of average total molecular weight of about 420 had a solubility in alcohol of approximately 96%.

EXAMPLE IV 860 gm. gelatin was dissolved in 2,200 ml. water. 244 grams of potassium hydroxide dissolved in 500 ml. of water was added to the solution and the solution heated at 190°F. for approximately 1 hour. An aliquot of the liquor resulting from hydrolysis was subjected to the conventional Kjeldahl analysis and the Van Slyke test to determine the total and amino nitrogen content. The total nitrogen content of approximately 13.2% and the Van Slyke of 2.20% indicated a reduction in molecular weight of the proteins to an average value of about 420.

The pH of the hydrolyzed gelatin solution was reduced to 10.0 and 572 gm. of palmityl chloride was added over a period of 6 hours. Reaction is indicated by evolution of heat and a drop in pH. When the pH dropped below 9.0, sodium hydroxide in the form of a 25% solution was added to raise pH to within the range of 9.0 to 10.0.

Upon completion of the reaction, as evidenced by a constant pH of 9.0, 10% hydrochloric acid was added to adjust the pHof pH of solution to 6.0. The solution was filtered to remove insoluble material and the filtrate was adjusted to pH 3.0 with 10% hydrochloric acid solution. Finely divided solids form in the acidic solution. The solids were separated from the liquids by centrifugation. The solids were washed with acid solution of pH 3.0 and were dried by freezing drying technique. Recovery of 620 gm. of dry reaction product establishes a yield of approximately 72%, based upon the dry weight of gelatin starting material.

The reaction product having an average total molecular weight of about 540 had a solubility in ethyl alcohol at 20% by weight of concentration of approximately 98%.

TABLE I

| Fatty Acid | Chemical and Physical Properties of Fatty Acid Polypeptide-Condensation Products | | | Mol. Weight of Alcohol Soluble Reaction Product |
|---|---|---|---|---|
| | %N, Content of Alcohol Soluble Reaction Product | Alcohol Solubility of Dry Reaction Product | Properties of Dry Films of Alcohol Soluble Fraction | |
| | NaCH-Collagen Hydrolyzate | | | |
| Lauric | 9.2–11.0 | 99% | Satisfactory | 433–583 |
| " | <9.2 | 97 | Soft-Tacky | (unsatisfactory) |
| " | >11.0 | Max. 95 | Cracks and Flakes | (") |
| Myristic | 7.2–9.0 | 98 | Satisfactory | 386–486 |
| " | <7.2 | 99 | Soft-Tacky | (unsatisfactory) |

TABLE I-continued

| | Chemical and Physical Properties of Fatty Acid Polypeptide-Condensation Products | | | |
|---|---|---|---|---|
| Fatty Acid | %N, Content of Alcohol Soluble Reaction Product | Alcohol Solubility of Dry Reaction Product | Properties of Dry Films of Alcohol Soluble Fraction | Mol. Weight of Alcohol Soluble Reaction Product |
| '' | >9.0 | Max. 94 | Cracks & Flakes | ('') |
| Palmitic | 6.2–8.2 | 97 | Satisfactory | 389–489 |
| '' | <6.2 | 95 | Soft-Tacky | (unsatisfactory) |
| '' | >8.2 | Max. 90 | Cracks & Flakes | ('') |
| Stearic | 5.1–6.8 | 94 | Satisfactory | 392–467 |
| '' | <5.1 | 90 | Soft-Tacky | (unsatisfactory) |
| '' | >6.8 | Max. 80 | Cracks & Flakes | ('') |

The criticality of average total molecular weight of reaction products produced by calcium hydroxide hydrolysis of collagen proteins is illustrated by the following table II.

TABLE II

| | CaOH-Collagen Hydrolyzate | | | |
|---|---|---|---|---|
| Fatty Acid | %N. Content of Alcohol Soluble Reaction Product | Alcohol Solubility of Dry Reaction Product | Properties of Dry Films of Alcohol Soluble Fraction | Mol. Weight of Alcohol Soluble Reaction Product |
| Lauric | 11.3–12.0 | 94% | Satisfactory | 633–743 |
| '' | <11.3 | 98 | Soft-Tacky | (unsatisfactory) |
| '' | >12.0 | Max. 90 | Cracks & Flakes | ('') |
| Myristic | 10.0–11.1 | 99 | Satisfactory | 560–685 |
| '' | <10.0 | 99 | Soft-Tacky | (unsatisfactory) |
| '' | >11.1 | Max. 98 | Cracks & Flakes | ('') |
| Palmitic | 7.8–9.2 | 99 | Satisfactory | 464–564 |
| '' | <7.8 | 98 | Soft-Tacky | (unsatisfactory) |
| '' | >9.2 | Max. 90 | Cracks & Flakes) | ('') |
| Stearic | 5.7–7.7 | 88 | Satisfactory | 417–517 |
| '' | <5.7 | 94 | Soft-Tacky | (unsatisfactory) |
| '' | >7.7 | Max. 75 | Cracks & flakes | ('') |

The amide reaction products as prepared above may be incorporated in cosmetic compositions in various forms such as alcohol solutions or in the alcohol solution component of emulsions. The amide reaction products of this invention may be present in said alcohol solutions in amounts in the range between about 5% and 50% by weight.

Compositions containing the amide reaction products of this invention are skin compatible, being suitable for periodic use at short, i.e., daily or at most weekly, intervals as distinguished from hair drying or waving lotions which can only be used with longer intervals between hair treatments.

In the case of human hair grooming compositions, examples of agents which facilitate grooming of the hair and help to keep the hair in place include, e.g., castor oil, mineral oil, lower alkyoxypolyoxy lower alkylene glycols such as butoxypolyoxy propylene glycol, higher molecular weight copolymers of random mixtures of ethylene oxide and propylene oxide, esters of fatty acids such as isopropylmyristate or the coconut oil fatty acid ester of polyethylene glycol having an average molecular weight of about 400, polyhydric alcohols such as glycerol and propylene glycol gums such as gum tragacanth, and the like. It is preferred to employ those substantially non-volatile organic grooming agents which have a molecular weight above about 75 and preferably above about 200 and which contain an alcoholic hydroxyl group such as the aforementioned glycols polyhydric alcohols, polymerized alkylene oxides, and castor oil. The acyl amide polypeptide derivatives of this invention can be employed in conjunction with the foregoing organic hair grooming materials, in hair grooming preparations in an amount from about 0.5% to 65% and preferably about 2% to 50% by weight of the composition.

In the case of hair grooming compositions, resins such as polyvinyl pyrolidone and the other above mentioned agents are employed in an amount from about 1% to 60% and preferably about 2% to 40% by weight of the compositions. When used in conjunction with the alcohol soluble reaction products of the present invention, the reaction products replace about 10% to 50% of the agent.

Hair spray composition in accordance with the present invention may be prepared in various forms and may consist of one or more phases. The spray may be prepared as a clear, homogeneous single phase liquid such as an alcohol solution or aqueous alcoholic composition. The hair preparation may also contain adjuvant materials such as vitamins, hormones, lanolin, bactericides, etc. in compatible proportions.

Hair preparation according to the invention dispensable as a mist like spray by propellants exerting a gas pressure of the order of 20 to 30 psi gauge at 70°F. such as are illustrated by the following examples. The quantities are indicated by weight unless otherwise specified.

EXAMPLE V
HAIR SPRAY

| Component | Parts (by weight) |
|---|---|
| Ethyl alcohol (Anhydrous) | 27.6 |
| Product of Example 1 | 2.4 |
| Freon 11 | 45 |
| Freon 12 | 25 |

EXAMPLE VI
HAIR SPRAY

| Component | Parts (by weight) |
| --- | --- |
| Polyvinyl Pyrrolidone Resin | 2.4 |
| Ethyl Alcohol (Anhydrous) | 26.4 |
| Product of Example 11 | 1.2 |
| Freon 11 | 44.5 |
| Freon 12 | 25 |
| Perfume | 0.5 |

We claim:

1. An amide form of polypeptide derivative having utility as an agent substantially completely soluble in anhydrous ethyl alcohol and insoluble in water comprising a reaction product of a hydrolyzate of proteins selected from the group consisting of alkali metal hydrolyzate and calcium hydroxide hydrolyzate having chemically bonded thereto through amide linkages to free -NH$_2$ groups on said hydrolyzate derived from a fatty acid reactant, an acyl radial selected from the group consisting of those having 12, 14, 16 and 18 carbon atoms, substantially all of said acyl radical being so bonded, said reaction product having an average total molecular weight of approximately 433 to 583 when prepared from an alkali metal hydrolyzate and having a 12 carbon atom acyl radical, having an average total molecular weight in the range of 386 to 486 when prepared from an alkali metal hydrolyzate and having a 14 carbon atom acyl radical, having an average total molecular weight in the range of 389 to 489 when prepared from an alkali metal hydrolyzate and having a 16 carbon atom acyl radical, having an average total molecular weight in the range of 392 to 467 when prepared from an alkali metal hydrolyzate and having an 18 carbon atom acyl radical and having an average total molecular weight in the range of 633 to 743 when prepared from a calcium hydroxide hydrolyzate and having a 12 carbon atom acyl radical, having an average total molecular weight in the range of 560 to 686 when prepared from a calcium hydroxide hydrolyzate and having a 14 carbon atom acyl radical, having an average total molecular weight in the range of 464 to 564 when prepared from a calcium hydroxide hydrolyzate and having a 16 carbon atom acyl radical and having an average total molecular weight in the range of 417 to 517 when prepared from a calcium hydroxide hydrolyzate and having an 18 carbon atom acyl radical.

2. The method of preparing an acyl amide form of polypeptide derivative, substantially completely soluble in anhydrous ethyl alcohol and insoluble in water and having utility as a grooming agent in aliphatic alcohol base compositions which comprises chemically bonding through amide linkages to free -NH$_2$ groups an acyl radical selected from the group consisting of those having 12, 14, 16 and 18 carbon atoms by reaction of a fatty acid halide containing said acyl radical in an alkaline aqueous solution of hydrogen ion concentration in the pH range between 7.5 and 12.5 with a hydrolyzate resulting from hydrolysis of proteins with an alkaline agent selected from the group of alkali metal hydroxide and calcium hydroxide and having an average molecular weight such that the reaction product has average total molecular weight of approximately 433 to 583 when prepared from an alkali mtal hydrolyzate and having a 12 carbon atom acyl radical, having an average total molecular weight in the range of 386 to 486 when prepared from an alkali metal hydrolyzate and having a 14 carbon atom acyl radical, having an average total molecular weight in the range of 389 to 489 when prepared from an alkali metal hydrolyzate and having a 16 carbon atom acyl radical, having an average total molecular weight in the range of 392 to 467 when prepared from an alkali metal hydrolyzate and having an 18 carbon atom acyl radical and having an average total molecular weight in the range of 633 to 743 when prepared from a calcium hydroxide hydrolyzate and having a 12 carbon atom acyl radical, having an average total molecular weight in the range of 560 to 686 when prepared from a calcium hydroxide hydrolyzate and having a 14 carbon atom acyl radical, having an average total molecular weight in the range of 464 to 564 when prepared from a calcium hydroxyde hydrolyzate and having a 16 carbon atom acyl radical, having an average total molecular weight in the range of 417 to 517 when prepared from a calcium hydroxide hydrolyzate and having an 18 carbon atom acyl radical, separating the reaction products from unreacted fatty acid halide and unreacted hydrolyzate in the reaction mixture by adjusting the pH of said reaction mixture to between about 5 and 6.5 to remove unreacted fatty acid halide, then adjusting the pH of the remaining reaction mixture to between 2 and 4 to precipitate the reaction products, washing the precipitated reaction products with water to remove water soluble contaminants, including unreacted polypeptides and thereafter drying the precipitate, isolating the alcohol soluble portion of the precipitate by mixing it with ethyl alcohol and recovering the reaction product solute from the alcohol solution.

3. The method according to claim 2 wherein the fatty acid reactant is added in an amount constituting a stoichiometric equivalent amount or up to 10% excess over the stoichiometric amount based upon the free amino groups of the hydrolyzate, the pH of the reaction mixture is maintained in the range between 7.5 and 12.5 until reaction is indicated as complete by a nonchanging pH, the temperature of the reaction mixture is maintained in the range between about 70°F. and 180°F., the pH of the reaction mixture is subsequently adjusted to about 6 to precipitate unreacted components from the solution of reaction products, the precipitated components are separated from the solution of reaction products, the pH of the solution of reaction products is adjusted to between 2 and 4 to precipitate the reaction products separating the precipitated reaction products from the resultant solution, and washing the precipitated products to remove water soluble contaminates, the washed precipitated products are dehydrated, the dehydrated products are mixed with aliphatic alcohol, the alcohol insoluble components are separated from the alcohol solution, the alcoholic solution of reaction product is utilized as the alcohol solution or the soluble reaction product components are recovered from the alcohol solution.

* * * * *